(12) United States Patent
Montague et al.

(10) Patent No.: US 11,529,526 B1
(45) Date of Patent: Dec. 20, 2022

(54) AUTOMATED EXTERNAL DEFIBRILLATOR

(71) Applicant: HeartHero, Inc., Denver, CO (US)

(72) Inventors: Gary Montague, Denver, CO (US); Anthony Verdeja, Denver, CO (US)

(73) Assignee: HeartHero, Inc., Denver, CO (US)

( * ) Notice: Subject to any disclaimer, the term of this patent is extended or adjusted under 35 U.S.C. 154(b) by 0 days.

(21) Appl. No.: 17/548,193

(22) Filed: Dec. 10, 2021

(51) Int. Cl.
*A61N 1/39* (2006.01)

(52) U.S. Cl.
CPC ......... *A61N 1/3904* (2017.08); *A61N 1/3937* (2013.01); *A61N 1/39046* (2017.08); *A61N 1/3975* (2013.01)

(58) Field of Classification Search
CPC .............. A61N 1/3904; A61N 1/39046; A61N 1/3937; A61N 1/3975
See application file for complete search history.

(56) References Cited

U.S. PATENT DOCUMENTS

| | | | |
|---|---|---|---|
| 5,713,925 A * | 2/1998 | Sullivan | A61N 1/3931 607/148 |
| 5,817,151 A | 10/1998 | Olson et al. | |
| 5,871,505 A | 2/1999 | Adams et al. | |
| 5,908,443 A | 6/1999 | Brewer et al. | |
| 6,353,758 B1 | 3/2002 | Gliner et al. | |
| 6,456,877 B1 | 9/2002 | Fishier | |
| 6,539,255 B1 | 3/2003 | Brewer et al. | |
| 8,615,295 B2 | 12/2013 | Savage et al. | |
| 9,026,147 B2 | 5/2015 | Galvin et al. | |
| 10,029,109 B2 | 7/2018 | Beyer et al. | |
| 10,071,256 B2 | 9/2018 | Montgomery et al. | |
| 10,112,054 B2 | 10/2018 | Beyer et al. | |
| D835,790 S | 12/2018 | Mercado et al. | |
| D836,202 S | 12/2018 | Andrews et al. | |
| 10,226,615 B2 | 3/2019 | Lang et al. | |
| 10,449,380 B2 | 10/2019 | Andrews | |
| 10,543,376 B2 | 1/2020 | Beyer et al. | |

(Continued)

FOREIGN PATENT DOCUMENTS

| | | |
|---|---|---|
| CN | 101745180 | 6/2010 |
| CN | 105013085 A | 11/2015 |

(Continued)

OTHER PUBLICATIONS

PCT Patent Application PCT/US2017/067442 International Search Report and Written Opinion dated Apr. 19, 2018.

(Continued)

*Primary Examiner* — Eric D. Bertram
(74) *Attorney, Agent, or Firm* — Avek IP, LLC

(57) ABSTRACT

An automated external defibrillator (AED) system includes shock generating electronics, a battery configured for providing power to the shock generating electronics, power management circuitry configured for controlling the shock generating electronics and the battery, and a controller configured for controlling the power management circuitry. The AED system is housed in a small enclosure that provides a hand-carryable device, and the enclosure includes an externally mounted clip that enables the device to be wearable on a user's belt. Cardiac pads are stored separately and are plugged into the device to automatically power on the device. An associated AED method is designed for a trained user to operate the AED system.

17 Claims, 9 Drawing Sheets

(56) References Cited

U.S. PATENT DOCUMENTS

| | | | |
|---|---|---|---|
| 10,565,845 B1 | 2/2020 | Beyer et al. | |
| 10,580,280 B1 | 3/2020 | Picco et al. | |
| 10,621,846 B1 | 4/2020 | Beyer et al. | |
| 10,665,078 B1 | 5/2020 | Picco et al. | |
| D893,032 S | 8/2020 | Smith et al. | |
| 10,737,105 B2 | 8/2020 | Andrew et al. | |
| 10,773,091 B2 | 9/2020 | Andrews et al. | |
| 10,799,709 B2 | 10/2020 | Teber et al. | |
| 11,103,718 B2* | 8/2021 | Montague | A61N 1/39044 |
| 2004/0015191 A1 | 1/2004 | Otman et al. | |
| 2004/0143297 A1 | 7/2004 | Ramsey | |
| 2004/0260376 A1 | 12/2004 | Craige et al. | |
| 2005/0244709 A1 | 11/2005 | Bucher | |
| 2007/0032830 A1 | 2/2007 | Bowers | |
| 2007/0218869 A1 | 9/2007 | Thijs | |
| 2007/0299473 A1 | 12/2007 | Matos | |
| 2009/0005827 A1* | 1/2009 | Weintraub | A61N 1/3904 601/84 |
| 2009/0240297 A1 | 9/2009 | Shavit et al. | |
| 2009/0254136 A1 | 10/2009 | Powers | |
| 2010/0070772 A1 | 3/2010 | Nakamura et al. | |
| 2010/0241181 A1 | 9/2010 | Savage et al. | |
| 2011/0071880 A1 | 3/2011 | Spector | |
| 2011/0152702 A1 | 6/2011 | Goto | |
| 2011/0190839 A1 | 8/2011 | Vaisnys et al. | |
| 2011/0224745 A1 | 9/2011 | Magruder | |
| 2012/0310315 A1 | 12/2012 | Savage et al. | |
| 2013/0012151 A1 | 1/2013 | Hankins | |
| 2013/0132465 A1 | 5/2013 | Brown | |
| 2014/0004814 A1 | 1/2014 | Elghazzaw | |
| 2014/0031885 A1 | 1/2014 | Elghazzawi et al. | |
| 2014/0039593 A1 | 2/2014 | Savage et al. | |
| 2014/0107718 A1 | 4/2014 | Foote et al. | |
| 2014/0243914 A1* | 8/2014 | Freeman | A61N 1/046 607/3 |
| 2014/0277227 A1* | 9/2014 | Peterson | A61N 1/3987 607/7 |
| 2014/0317914 A1 | 10/2014 | Shaker | |
| 2016/0220833 A1* | 8/2016 | Tan | A61N 1/046 |
| 2016/0271408 A1 | 9/2016 | Newton et al. | |
| 2017/0157415 A1 | 6/2017 | Horseman et al. | |
| 2017/0325091 A1 | 11/2017 | Freeman | |
| 2018/0161586 A1 | 6/2018 | Beyer et al. | |
| 2018/0161588 A1 | 6/2018 | Montgomery et al. | |
| 2018/0161589 A1 | 6/2018 | Beyer et al. | |
| 2018/0161591 A1 | 6/2018 | Andrews et al. | |
| 2018/0169426 A1* | 6/2018 | Montague | G16H 40/63 |
| 2018/0243573 A1 | 8/2018 | Yoder | |
| 2019/0044362 A1 | 2/2019 | Beyer et al. | |
| 2019/0111272 A1* | 4/2019 | Hochhalter | A61N 1/3925 |
| 2019/0117983 A1 | 4/2019 | Andrews et al. | |
| 2019/0117984 A1 | 4/2019 | Andrews et al. | |
| 2019/0117987 A1 | 4/2019 | Beyer et al. | |
| 2019/0117988 A1 | 4/2019 | Beyer et al. | |
| 2019/0117989 A1 | 4/2019 | Andrews et al. | |
| 2019/0143131 A1* | 5/2019 | Webster | A61N 1/3993 607/7 |
| 2019/0329056 A1 | 10/2019 | Sjoquist | |
| 2019/0329062 A1 | 10/2019 | Andrews et al. | |
| 2019/0329257 A1 | 10/2019 | Teber et al. | |
| 2019/0356492 A1 | 11/2019 | Picco et al. | |
| 2020/0085333 A1 | 3/2020 | Freed et al. | |
| 2020/0090483 A1 | 3/2020 | Picco et al. | |
| 2020/0092700 A1 | 3/2020 | Picco et al. | |
| 2020/0094038 A1 | 3/2020 | Andrews | |
| 2020/0094039 A1 | 3/2020 | Andrews | |
| 2020/0094044 A1 | 3/2020 | Andrews et al. | |
| 2020/0108261 A1 | 4/2020 | Beyer et al. | |
| 2020/0143651 A1 | 5/2020 | Beyer et al. | |
| 2020/0152037 A1 | 5/2020 | Picco et al. | |
| 2020/0215346 A1 | 7/2020 | Sturman et al. | |
| 2020/0221263 A1 | 7/2020 | Sturman et al. | |
| 2020/0242907 A1 | 7/2020 | Beyer et al. | |
| 2020/0286352 A1 | 9/2020 | Beyer et al. | |
| 2020/0286353 A1 | 9/2020 | Jafri et al. | |
| 2020/0398066 A1 | 12/2020 | Teber et al. | |
| 2021/0316152 A1 | 10/2021 | Sturman et al. | |
| 2022/0072322 A1 | 3/2022 | Montague et al. | |

FOREIGN PATENT DOCUMENTS

| | | |
|---|---|---|
| CN | 108671401 A | 10/2018 |
| CN | 111539866 A | 8/2020 |
| DE | 202004002106 U1 | 6/2004 |
| EP | 1157717 B1 | 1/2005 |
| EP | 2218478 A1 | 8/2010 |
| EP | 2450082 A1 | 5/2012 |
| EP | 3506981 A1 | 7/2019 |
| EP | 2879759 B1 | 10/2019 |
| EP | 3551285 A1 | 10/2019 |
| EP | 3681597 A1 | 7/2020 |
| JP | 2020503916 A | 2/2020 |
| JP | 2020524058 A | 8/2020 |
| KR | 102152282 A | 2/2016 |
| KR | 20160012239 A | 2/2016 |
| KR | 101780214 B1 | 10/2017 |
| WO | 2001010496 A2 | 2/2001 |
| WO | 2007069162 A1 | 6/2007 |
| WO | 2007135599 A2 | 11/2007 |
| WO | 2008057302 A2 | 5/2008 |
| WO | 2010066014 A2 | 6/2010 |
| WO | 2010146492 A1 | 12/2010 |
| WO | 2015143460 A1 | 10/2015 |
| WO | 2016092800 A1 | 6/2016 |
| WO | 2016149680 A1 | 9/2016 |
| WO | 2018111688 A1 | 6/2018 |
| WO | 2018232450 A1 | 12/2018 |
| WO | 2019070516 A1 | 4/2019 |
| WO | 2020055676 A1 | 3/2020 |
| WO | 2020056028 A1 | 3/2020 |
| WO | 2020068997 A1 | 4/2020 |
| WO | 2020142662 A1 | 7/2020 |

OTHER PUBLICATIONS

Automated External Defibrillators—NewAEDs—AED.com, www.aed.com/new-aeds.html. Retrieved Sep. 14, 2018.

How Corpuls Works, Always Very Close to the User, https://corpuls.world/, Copyright 2017, Retrieved Sep. 14, 2018.

Heartsmart.com, Defibtech Lifeline AED, www.heartsmart.com/defibtech-lifeline-aed-defibrillator-p/dcf-100.htm, Copyright 2015, Retrieved Sep. 14, 2018.

Schiller The Art of Diagnostics, The World's First Pocket Defibrillator Fred Easyport, www.schiller.ch/ca/us/product/fred-easyport. Retrieved Sep. 14, 2018.

Phillips, HeartStart FRx Automated External Defibrillator, www.usa.philips.com/healthcare/product/HC861304/heartstart-frx-automated-external-defibrillator. Copyright 2004-2018, Retrieved Sep. 14, 2018.

Phillips, Heartstart OnSite AED, Product No. M5066A, www.usa.philips.com/healthcare/product/HCM5066A/heartstart-onsite-aed. Copyright 2004-2018, Retrieved Sep. 14, 2018.

Physio Control, Product Overview, www.physio-control.com/ProductsPrehospital.aspx, Copyright 2018, Retrieved Sep. 14, 2018.

Extended European search report (EESR) dated Jul. 10, 2020.

"AED Plus Technical Specifications", Dec. 31, 2011; Retrieved from the Internet: URL:https://web.archive.org/web/20120526132350if_/http://zoll.com/uploadedFiles/Public_Site/Products/AED_Plus/AED PlusSpecSheet.pdf; Retrieved on Jun. 30, 2020.

Okamura et al, "Evaluation of a Unique Defibrillation Unit with Dual-Vector Biphasic Waveform Capabilities: Towards a Miniaturized Defibrillator", Pace, Published Feb. 2017, pp. 108-114, vol. 40.

Dames, J.S., "Monophasic vs Biphasic Waveform Defibrillation," AED Superstore Website, published on Mar. 3, 2016 [online], retrieved from <URL:https://www.aedsuperstore.com/resources/monophasic-vs-biphasic/ [retrieved on Aug. 14, 2019], 9 pages.

Cahn, Michelle, "Connecting Your IoT Platform to 911: RapidSOS Emergency API," RapidSOS Website, published on Det. 24, 2017 [online], retrieved from <URL:https://rapidsos.com/our-latest/product-

(56) References Cited

OTHER PUBLICATIONS spotlight-rapidsos-emergency-api/ [retrieved on Mar. 12, 2021], 3 pages.

* cited by examiner

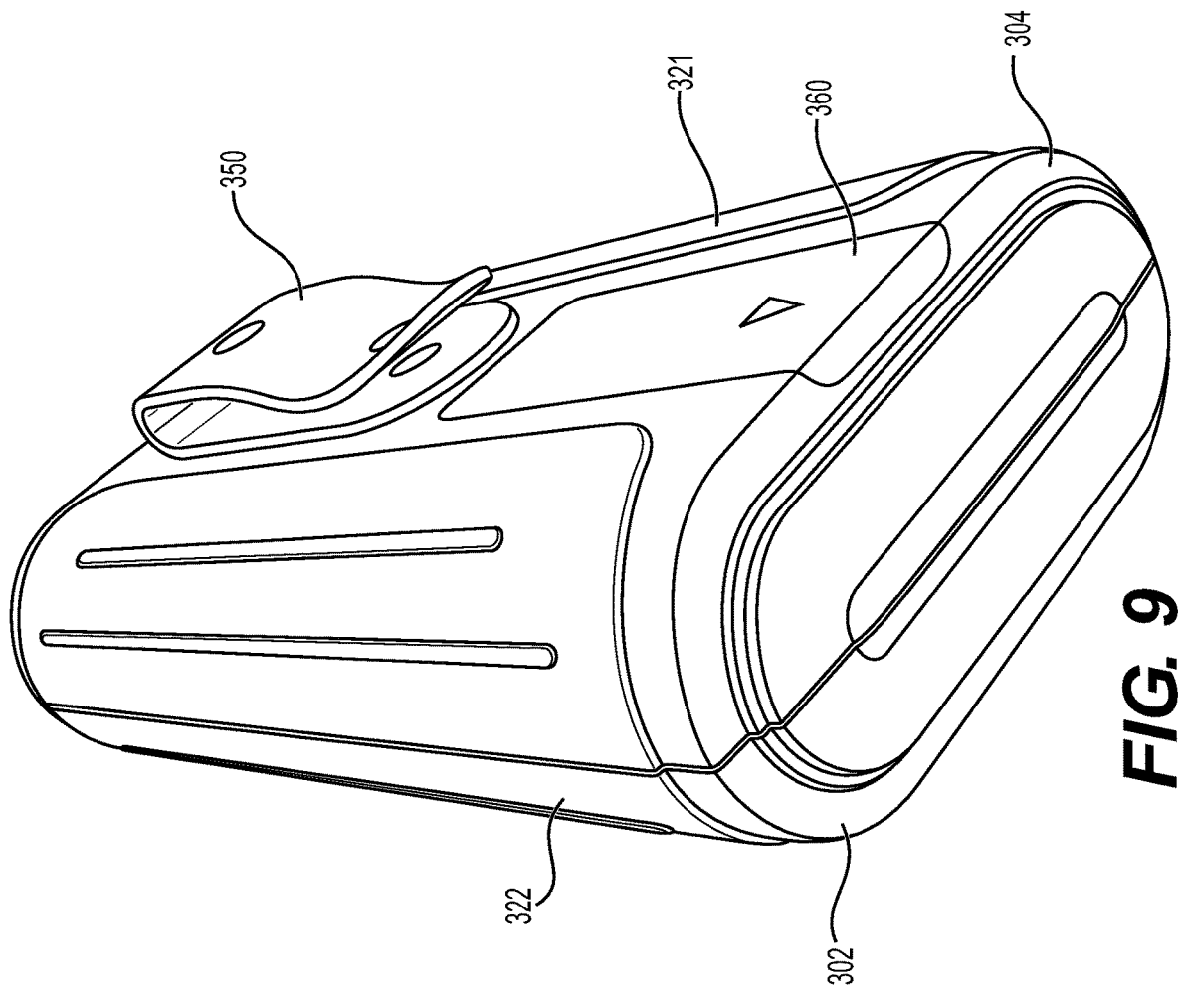

AUTOMATED EXTERNAL DEFIBRILLATOR

FIELD OF THE DISCLOSURE

Aspects of the present disclosure generally relate to automated external defibrillators (AEDs) and, more particularly, to compact AED systems and methods.

BACKGROUND OF THE DISCLOSURE 86 million Americans have risk factors for sudden cardiac arrest (SCA), while 12 million are at high risk. Cardiac events represent more deaths in America than breast, lung, colon and prostate cancer combined. More than 360,000 SCAs occur outside of the hospital each year. According to the American Heart Association, nearly 70 percent of these SCAs occur at home, out of reach of the lifesaving shock of an AED.

As each minute passes following a SCA, the chances of survival decrease significantly. If an AED is not applied within 10 minutes of a SCA event, chances of survival decrease to less than 1%.

One approach to increasing the chance of survival for SCA sufferers is to make AEDs more readily available and accessible for more people. However, the AEDs currently available on the market tend to be heavy, not portable, expensive, and intimidating to use for people without medical training. For example, U.S. Pat. No. 11,103,718, entitled "Automatic External Defibrillator Device and Methods of Use," which disclosure is incorporated herein in its entirety by reference, provides a possible solution to overcome the availability and accessibility problem by providing a compact AED device suitable for portability.

Aspects of the present disclosure provide techniques and structures that improve the performance of AEDs suitable for high portability applications.

SUMMARY OF THE DISCLOSURE

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

In some aspects, the techniques described herein relate to an automated external defibrillator (AED) system, including: shock generating electronics configured to provide at least one electrical shock suitable for a patient experiencing a cardiac event; a battery configured for providing power to the shock generating electronics; power management circuitry configured for managing the shock generating electronics and the battery; a single microprocessor configured for controlling the power management circuitry; an enclosure configured to house the shock generating electronics, the battery, the power management circuitry, and the single microprocessor; and a clip mounted to an exterior of the enclosure, wherein the clip is configured for clipping the AED system to a user's belt for carrying the AED system.

In some aspects, the techniques described herein relate to a method for using an external defibrillator (AED) system, the AED system including shock generating electronics, a single battery configured for providing power to the shock generating electronics, power management circuitry configured for managing the shock generating electronics and the battery, and a single microcontroller configured for controlling the power management circuitry, an enclosure and a clip mounted to an exterior of the enclosure, the method including: plugging cardiac pads into a connector on the exterior of the enclosure; automatically powering on the AED system when the cardiac pads are plugged into the connector; monitoring a charge status of the battery; monitoring vital signs via the cardiac pads; charging the shock generating electronics; determining whether a shockable rhythm exists; and administering a shock to a patient experiencing a cardiac event via the cardiac pads when the shockable rhythm exists.

BRIEF DESCRIPTION OF THE DRAWINGS

Embodiments of the invention are described in detail below with reference to the attached drawing figures, wherein:

FIG. 9 is yet another perspective view of the AED of FIG. 3 showing the back side and a bottom end.

Figure 1:
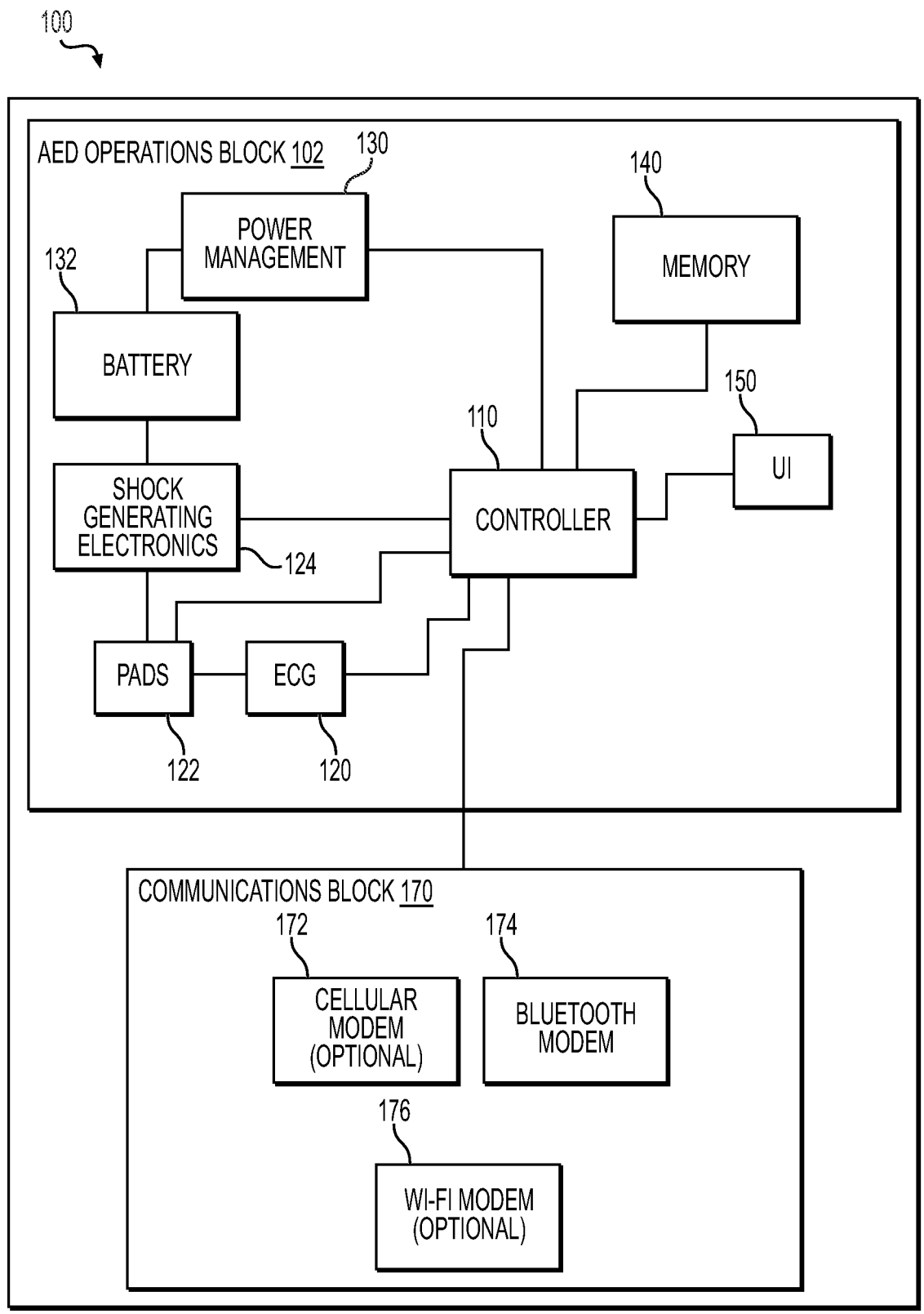
FIG. 1 illustrates a block diagram of an exemplary AED, including an AED operations block and a communications block, in accordance with an embodiment.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized, and changes can be made without departing from the scope of the invention. The following detailed description is, therefore, not to be taken in a limiting sense. The scope of the invention is defined only by the appended claims, along with the full scope of the equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

If more AEDs can be made available to more people, with improved portability, lower cost, and enhanced ease of use, then more lives can be saved in the event of a cardiac event, such as a sudden cardiac arrest (SCA), occurring outside of a hospital setting. That is, like an EpiPen® injector is prescribed for and carried by those diagnosed with potentially life-threatening allergies, a portable AED can be a necessary and routine item prescribed to those diagnosed as being at risk for SCA. A portable, affordable, and user-friendly AED with safe and simple application protocol is desired for such wide-spread proliferation of AEDs in the consumer market. Additionally, a device that is small and light enough to be worn or carried by emergency personnel is desired so that a life-saving shock may be administered in the field (e.g., prior to moving a patient to an ambulance).

In embodiments described herein, many features not required for use of the device are removed to achieve further reduction in size and weight of the device. For example, a graphic user interface (GUI), which provides helpful guidance for an untrained user, is omitted from AED 100. Instead, in some embodiments, AED 100 is configured for operation by a trained user. For example, a professional responder or emergency personnel, such as an Emergency Medical Technician (EMT), police officer, fire fighter, etc., may be trained in the safe operation of AED 100 without needing a GUI or other non-essential features. Additionally, AED 100 may be configured with a minimal amount of battery power. For example, AED 100 may include only enough batteries to achieve a single charge for delivery of a single shock to a patient within a predetermined timeframe, as opposed to larger portable AEDs having enough battery capacity to provide a multi-shock protocol (e.g., a protocol designed to provide multiple shocks to a patient). In embodiments, AED 100 includes a single battery. The single battery is, for example, a commercially available household battery such as a CR123 battery. In embodiments, AED 100 may charge shock generating electronics 124 via a single CR123 battery in 90 to 120 seconds.

An exemplary embodiment of the AED includes: (1) a defibrillator including a battery to charge a capacitor to store and deliver an electric shock; (2) a communication module to transmit and receive data via a wireless connection; and (3) cardiac pads with electrodes to detect and monitor chest wall compression depth, compression rate, and chest wall impedance, and heart rhythm; and (4) a smartphone or mobile device application to analyze information received from the cardiac pads and recommend appropriate therapy, the application also having the ability to contact EMS via the smartphone/mobile device with GPS, Wi-Fi and/or cellular capabilities. In certain embodiments, these components are connected as follows: a smartphone with application is connected to the defibrillator via either a wired or wireless connection, such as Bluetooth® or Wi-Fi, then at least two electrodes with wires ending in cardiac pads connect from the battery/capacitor pack to the patient's chest.

Certain embodiments include one or more of the following: (1) the AED connects to a mobile device (e.g., smartphone) via a wired or wireless connection (e.g., Bluetooth®, Wi-Fi), or through a microphone; (2) the charge for the defibrillating shock is generated from a replaceable source (e.g., battery); (3) the AED includes a control module, at least one capacitor and ability to detect and deliver any range of electrical shock; (4) the system components and application detect the impedance of the victim's chest wall and cardiac pad placement; (5) given impedance information, the system and application automatically recommends or configures an electrical charge for the cardiac event patient; (6) the cardiac pads can be placed anywhere on the body of the cardiac event patient; (7) the cardiac pads detect the force of cardiopulmonary resuscitation (CPR) compressions on the SCA patient using, for example, a pressure sensor, impedance detector and/or accelerometer; (8) the mobile device (e.g., smartphone) may be configured to interface with multiple other medical devices via wired or wireless connections (e.g., Bluetooth® or Wi-Fi) or microphone; (9) the mobile device is configured to receive data from the AED, which may be used to monitor vital signs on the cardiac event patient including, but not limited to, blood pressure, heart rate, oxygen saturation, temperature, respiratory rate, capnography, and electrical cardiac activity; (10) the AED has two or more electrodes (e.g., cardiac pads) that connect to the patient; (11) the mobile device/AED/electrode combination provides a 12-lead electrocardiography (ECG) output; (12) the AED is brand agnostic with respect to the mobile device or operating system; (13) the mobile device may be paired via wireless communications or connect via wire to multiple medical devices simultaneously; (14) the mobile device communicates with EMS via an automated voice annunciation via cellular network, video, SMS or any other modality by which EMS is able to receive information; (15) information given to EMS includes, but is not limited to, current vital signs, CPR results, detectable cardiac rhythm, number of shocks given, and GPS coordinates/geolocation of events in progress; (16) such information is generated on a periodic basis and transmitted to incoming EMS, or generated upon request by EMS via the mobile device application; (17) EMS is able to access the mobile device application on a separate paired mobile device, facilitating AED location and data requests therefrom; (18) the mobile device application allows the AED controller to be paired with the information system used by EMS, thus allowing the remote administration of cardiac shock (e.g., if a child is using the AED for an adult); (19) the associated mobile device and software application may guide a user for proper cardiac pad placement; (20) the associated mobile device and software application suggest confirmation of no pulse if an optional onboard photoplethysmography (PPG) sensor does not detect a pulse; (21) the associated mobile device provides guidance using industry standard for timing of delivery of shock and CPR; and (22) the associated mobile device automatically contacts EMS if no call to emergency services is manually initiated after delivery of first shock.

Certain embodiments described herein include one or more of the following: (1) use one or more batteries that can be purchased off-the-shelf; (2) include specialized capacitors and circuitry that generate a therapeutic charge from the off-the-shelf battery; (3) continuously analyze the cardiac rhythm during CPR; (4) include sensors in the cardiac pads to detect impedance of the chest wall and ensure proper pad connection; (5) include additional sensors in the cardiac pad to monitor compression force, rate and depth of CPR; (6) by using the sensors to monitor vital signs, ensure that a cardiac shock is not given at an undesired time; and (7) via the sensors inside the cardiac pad, communicate information to the software system regarding size of chest wall which then allows for determination of a therapeutic shock that is correlated with the size of victim and their individual anatomy.

Similarly, the associated method described herein provide the following: (1) the mobile device software application gives the ability to call emergency services (such as 911 in the United States) and assist the bystander in providing effective CPR; (2) the mobile device software application is able to upload and record data of the resuscitation efforts such as, but not limited to, vital signs, cardiac rhythm, quality of CPR, and outcome of electric shock. Certain embodiments also transmit data to from the AED to as associated mobile device in real-time or after the fact.

Certain embodiments of the present invention provide the following: (1) the AED runs off of one or more readily commercially available consumer batteries; (2) the AED connects to a mobile device and is small enough for everyday portability; and (3) includes cardiac pads that can detect force, rate, and depth of compression along with impedance of chest wall.

Furthermore, the processes associated with certain embodiments of the invention provide the following: (1) the AED is wearable so that an EMT or other trainer user may have the AED on their person at all times while on duty; (2) the software application confirms for a trained user that quality CPR is being performed by using the data obtained from the cardiac pads, such as compression depth, compression rate, and placement of hands; (3) the AED uses the data to prompt the user if the cardiac pads need to be checked or re-applied or if the CPR technique needs to be modified; (4) a software application detects the cardiac rhythm during active chest compression; (5) the software application analyzes cardiac rhythm and provides electric shock for appropriate cardiac arrhythmias; and (6) the user will be prompted to stop CPR upon return of spontaneous circulation (ROSC).

It is still further an objective of certain embodiments of the present invention to provide an automated external defibrillator device that is cost effective, thus increasing the use of AEDs and thereby saving lives.

Further still, it is an objective of certain embodiments of the present invention to provide a device that is smaller and more lightweight than other solutions, thereby enabling the device to be easily portable and wearable. Certain embodiments have a weight of less than one pound. By making it more portable it increases accessibility, thus the product will be utilized more frequently, ultimately saving more lives.

In an embodiment, a mobile device is connected via hardwire, Bluetooth® or Wi-Fi to a case that holds the battery, specialized capacitors, and circuitry. At least two cardiac pads with sensors are stored separately and connected via wire to the AED when needed. The case protects the user from the risk of electrical shock and protects the internal electronics from electrostatic discharge (ESD), which can cause the electronics to fail or malfunction in an unsafe way. Suitable materials for the case may include a variety of plastics and other insulating materials.

Connecting the AED to a mobile device is done via wire to a connection port on the mobile device or via a wireless mechanism such as Bluetooth® or Wi-Fi. The mobile device includes software for receiving input via wire or wireless connection from the AED. The mobile device application can automatically send the patient's information including, but not limited to, vital signs and cardiac rhythm to a nearby hospital or regional medical center. The mobile device application can guide the user regarding correct depth and rate of compression and be able to advise cardiac shock. The AED case holds a portable battery, capacitors, and circuitry to generate and store at least one electrical charge to produce a therapeutic charge to cardiovert a patient in cardiac arrhythmia with the goal of return of spontaneous circulation (ROSC). The cardiac pads are not connected to the AED case when the AED is not in use. Prior to use, the cardiac pads are connected to the AED by the user via hardwires, as further described below in connection with the drawing figures. The cardiac pads are able to detect cardiac rhythm when active CPR is taking place. As an example, the cardiac pads have sensors embedded that will be able to detect rate and depth of compressions of the bystander providing CPR. The sensors in the cardiac pads send information back to the controller of the AED, and optionally to a mobile device application, for analysis of shockable versus non-shockable cardiac rhythm. The cardiac pads are used to deliver the therapeutic shock to the heart. The cardiac pads detect impedance of the chest to allow the application to calculate the correct therapeutic electric shock dosage and also ensure the cardiac pads have the proper connection on the patient to increase the best chance of cardioverting.

FIG. 1 is a block diagram of an exemplary AED 100 including an AED operations block 102 and a communications block 170, in accordance with an embodiment. AED operations block 102 includes various components that enable AED 100 to generate and deliver, within regulatory guidelines, an electric shock to a person experiencing a cardiac event. Exemplary cardiac invents include but are not limited to sudden cardiac arrest (SCA), rapid atrial fibrillation or ventricular tachycardia. As shown in the embodiment illustrated in FIG. 1, AED operations block 102 includes a controller 110, which controls a variety of components including an electrocardiogram (ECG) monitoring circuitry 120, which is in turn connected with cardiac pads 122. Cardiac pads 122 are configured for attachment to specific locations on a patient experiencing a cardiac event for delivering an electric shock to the patient. In embodiments, cardiac pads 122 are configured to receive ECG signals from the patient in addition to administering the electric shock. In some embodiments, cardiac pads 122 are waterproof. The cardiac pads 122 may be configured for reuse a predetermined number of times, after which the cardiac pads are replaced. The ECG signals are transmitted from cardiac pads 122 to ECG monitoring circuitry 120, which is communicatively coupled with controller 110.

Shock generating electronics 124 are configured to charge a capacitor under control of controller 110. In embodiments, AED 100 comprises a flat square capacitor for fitting within the case or enclosure of AED 100, as further described below in connection with FIGS. 3-9. In embodiments, the shock generating electronics 124 are configured to provide a voltage waveform that is between about 20-360 Joules in total energy. The amount of energy produced is adjustable by amplitude of the current, polarity of the phase, and the peak Joules provided. A lower energy shock (i.e., lower peak Joules) may be applied for a longer duration to achieve a similar effect as a higher energy shock applied for a shorter duration. In certain embodiments, the shock generating electronics 124 include a quad-phasic truncated exponential power stage that is configured to produce a shock of about 23 Joules to reduce complexity and the size of the capacitor. In some embodiments, a biphasic shock of about 150 Joules is produced. In other embodiments, a monophasic shock of about 360 Joules is produced.

Controller 110 may include, for example, non-transitory memory for storing software instructions. The non-transitory memory may be communicatively coupled with a processor (e.g., microprocessor) for executing software instructions stored on the non-transitory memory. Software instructions may include, for instance, workflow information for operating AED 100, as described herein. Controller 110 is also connected with a memory 140, which stores information regarding AED 100, such as use history, battery status, shock administration and CPR protocols, and other information (e.g., stored in look-up tables) used in the operation of AED 100. Memory 140, may, in some embodiments, be used by controller 110 to instruct a user on CPR and/or shock administration via communications block 170. In embodiments, controller 110 is a single microcontroller or single microprocessor.

AED operations block 102 includes a power management block 130, which is also controlled by controller 110 in embodiments. Power management block 130 comprises power management circuitry configured for managing the power consumption by various components within AED operations block 102. For instance, power management block 130 monitors a charge status of a battery 132, which provides electrical power to shock generating electronics 124. Power management block 130 provides instructions for controlling the on/off status of all electrical components of AED 100 via controller 110 so as to minimize power consumption while AED 100 is not being used. For example, power management block 130 is configured to completely power down ECG monitoring circuitry 120 and shock generating electronics 124 when the AED is not being used. In embodiments, power management block 130 is configured to provide a signal to a user via controller 110 for notifying the user of a charge status of battery 132, as further described below.

Figure 3:
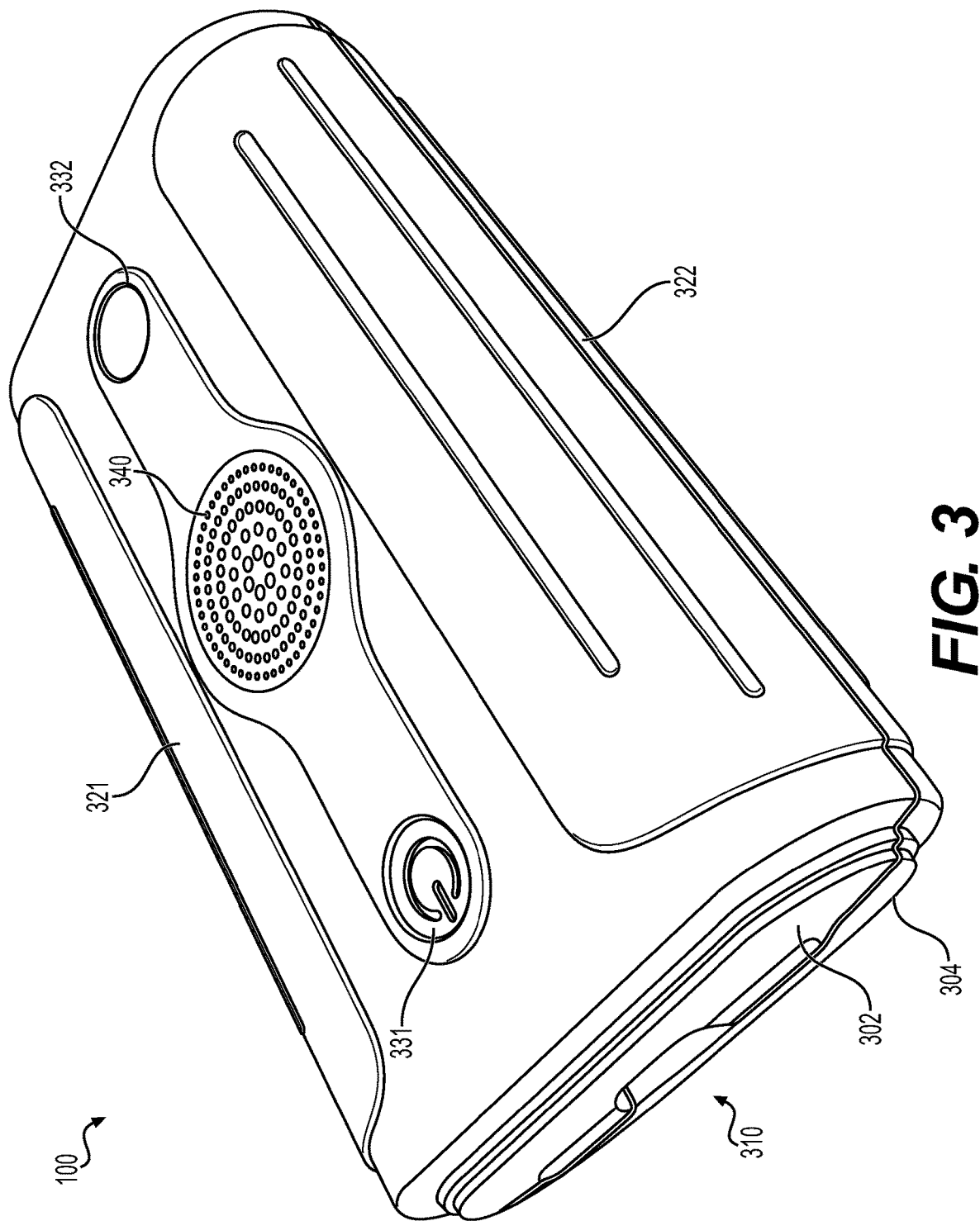
FIG. 3 is a perspective view of an exemplary AED showing a front side, in accordance with an embodiment.
Figure 4:
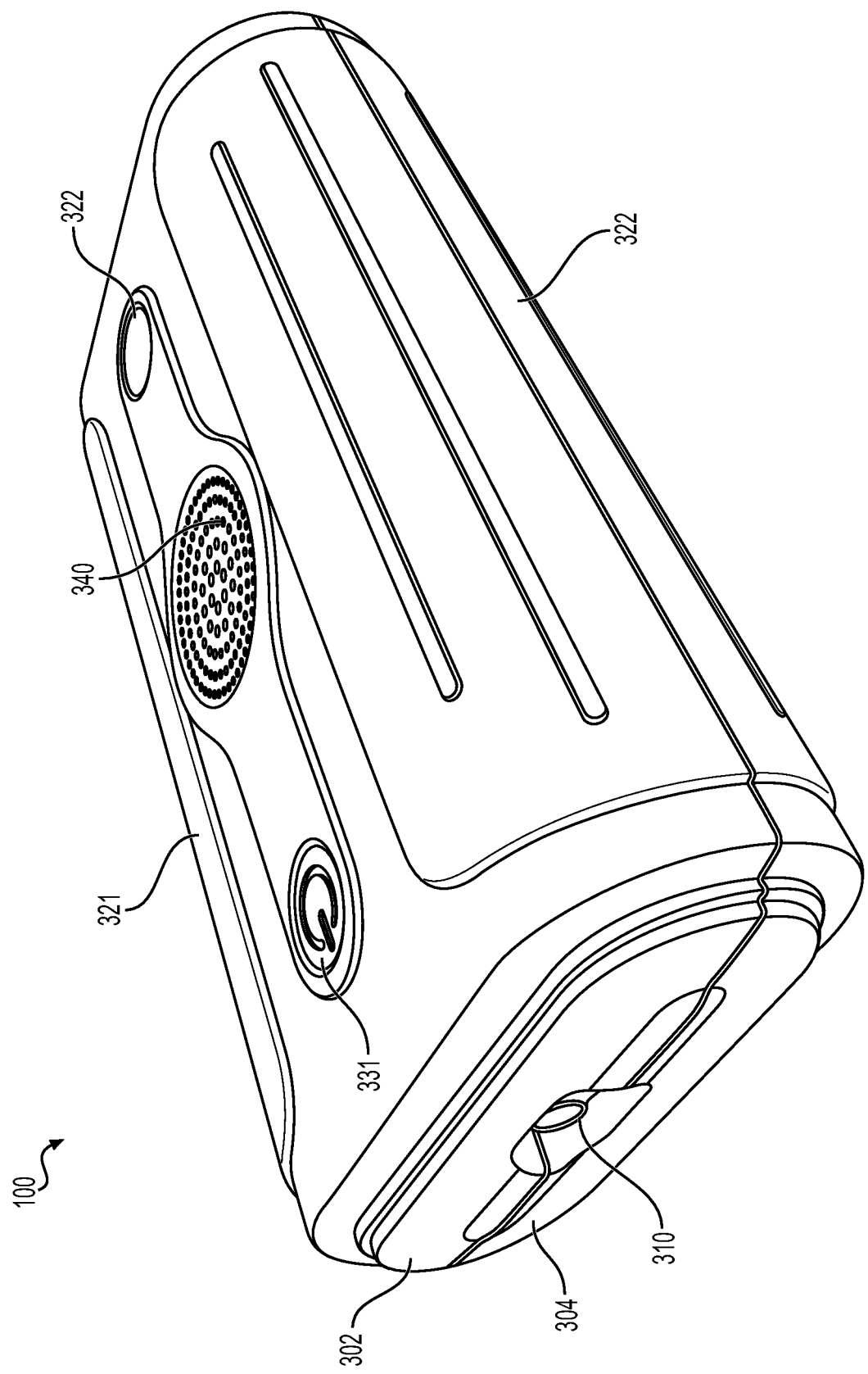
FIG. 4 is another perspective view the AED of FIG. 3 showing the front side.

A user-interface (UI) 150 is communicatively coupled with controller 110. In embodiments, UI 150 provides a simple user interface that minimizes space and electrical power requirements. For example, UI block 150 intentionally omits a graphic user interface such as a liquid crystal display (LCD) or touchscreen in order to reduce the size and complexity of AED 100. UI 150 may include a speaker to provide audible sounds (e.g., beeps) and/or voice prompts for aiding the AED user. For example, as shown in FIGS. 3 and 4, UI 150 may comprise a small speaker 340 (e.g., 27 mm diameter and 6.6 mm height) that is lightweight (e.g., about 9 g) and consumes a small amount of electrical power (e.g., 2 W or less).

UI 150 may include one or more push buttons for receiving input from a user. The one or more push buttons may be used to power AED 100 on or off, to request a charge status of the battery 132, to initiate charging of the shock generating electronics 124, or to administer a shock to a patient via cardiac pads 122, for example. For the embodiment shown in FIGS. 3-5, a first button 331 and a second button 332 are shown. For example, first button 331 may be a power on/off button, and in some embodiments, a battery status button. Second button 332 may be configured as a shock button. First and second buttons 331, 332 are further described below in connection with FIGS. 3-5.

UI 150 may also include one or more light indicators. A light source of UI 150 may include one or more light-emitting diodes (LEDs). Different color LEDs may be used (e.g., to indicate more than one status). Illumination of the LEDs is under control of controller 110, and therefore, the LEDs may be individually turned on or off to provide one or more blinking indicators. Additionally, the LEDs may each be dimmed via pulse-width modulation (PWM).

In embodiments, UI 150 comprises one or more lights associated with the one or more push buttons located on the exterior of AED 100 to provide indications associated with the one or more push buttons, respectively. The one or more lights associated with each push button may be located adjacent the push button or internal to the push button for illuminating the push button itself. The one or more lights may be brightly lit, dimly lit, or unlit under control of controller 110. Likewise, the one or more lights may be controlled to blink rapidly, slowly, or not at all via controller 110. Additionally, the one or more lights may be illuminated with different colors. For the embodiment described below in connection with FIGS. 3-5, lights may be employed to illuminate a first button 331 and a second button 332. For example, first button 331 may be illuminated to indicate a power status of AED 100 and/or a charge status of battery 132, and second button 332 may be illuminated to indicate a status of the shock generating electronics 124 while being charged. These examples are further described below in connection with FIGS. 3 and 4.

Still referring to FIG. 1, AED 100 includes a communications block 170, also controlled by controller 110. Communications block 170 provides connections to external systems and entities outside of the AED, such as emergency medical services, hospital emergency rooms, physicians, electronic health record systems, as well as other medical equipment, such as ventilators and an external ECG. Communications block 170 includes at least one of the following communication features: a cellular modem 172, a Bluetooth® modem 174, a Wi-Fi modem 176 for providing wireless connection to and from an external device. The various communication modes within communications block 170 are configured to comply with regulatory guidance related to wireless technology, such as coexistence, security, and electromagnetic compatibility. By having a single controller (e.g., a microprocessor) control communications block 170 within AED 100, the circuit design and firmware configuration of AED 100 is greatly consolidated over other AEDs with multiple processors, while enabling a reduction in power consumption of the device.

In embodiments, AED 100 is configured to be remotely controlled for providing telemedicine. For example, communication between a remote operator (e.g., an EMT or physician located at a hospital or regional medical center) may operate AED 100 via communications block 170. For example, a remote operator may provide instructions to AED 100 via cellular or Wi-Fi connection, or through a Bluetooth® paired device (e.g., smartphone). A local user turns on AED 100, connects the cardiac pads 122 to AED 100, and places the cardiac pads on the patient. The remote operator may be in communication with local user via cellular connection (directly through AED 100 or via a Bluetooth® paired or separate cellular phone) to facilitate placement of the cardiac pads, to assist with delivering CPR to the patient, etc. The remote operator may then transmit one or more signals to AED 100 via a smartphone or computer application to administer a shock to the patient. The remote operator may also monitor vital signs (e.g., ECG signals) of the patient that are received by AED 100.

In some embodiments, communications block 170 includes only a Bluetooth® modem 174, and AED 100 is configured to communicate with external systems and entities outside of the AED via a Bluetooth® paired device (e.g., a smartphone). In these embodiments, a Bluetooth® only arrangement further reduces the complexity, size, and power requirements of AED 100.

Figure 2:
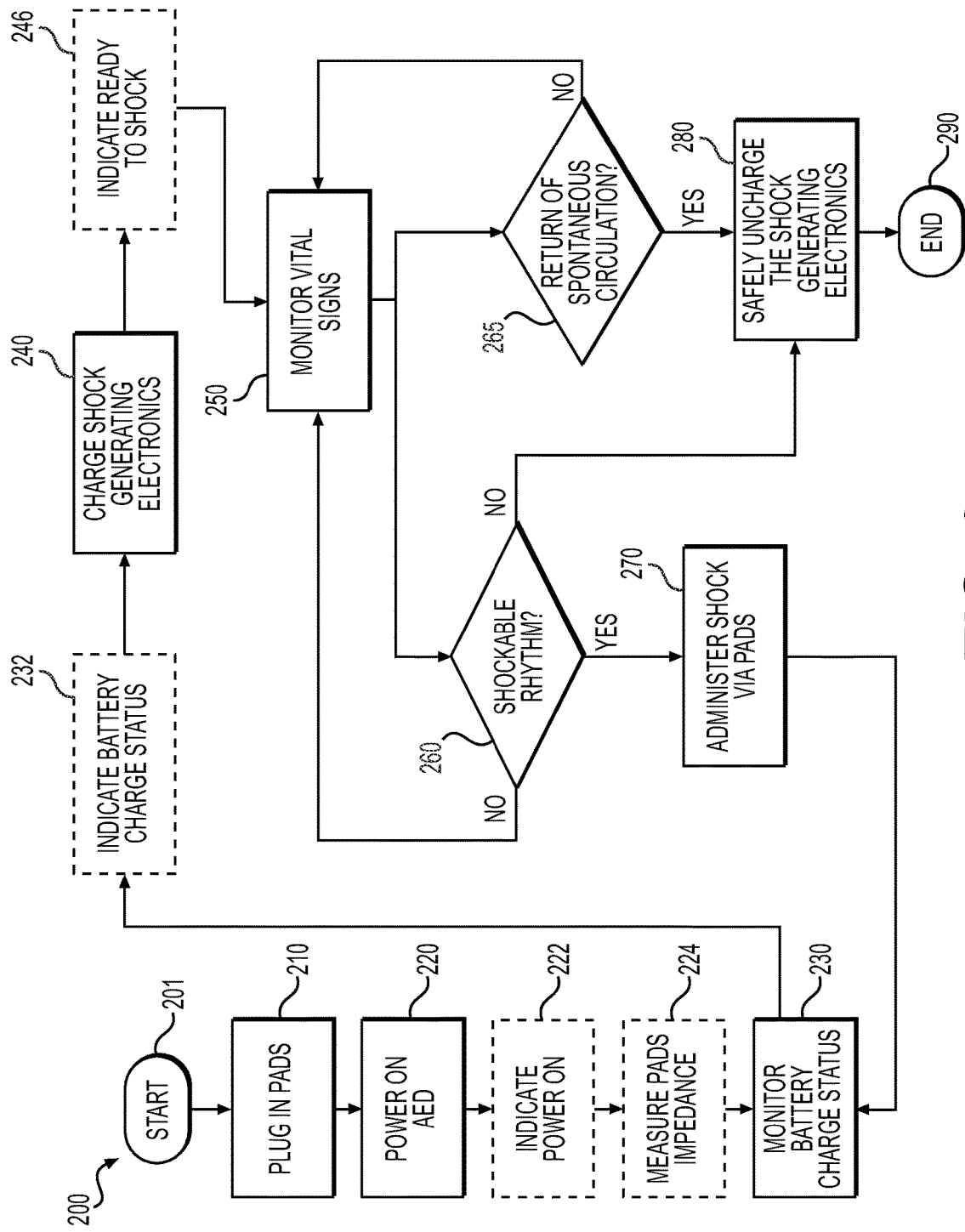
FIG. 2 illustrates a flow diagram of a method configured for use with the AED of FIG. 1, in accordance with an embodiment.

FIG. 2 provides an exemplary AED operation method 200 which is configured for use with AED 100 of FIG. 1, for example. Method 200 is configured for use by a trained operator. Method 200 starts at a step 201.

In a step 210, cardiac pads are plugged into the AED device. In some embodiments, AED 100 is configured for wearing or carrying by a trained user without having cardiac pads connected. Without the pads connected, AED 100 has a smaller profile and avoids having exposed wiring connected to AED 100 while the device is worn or carried, which prevents the wires from getting caught or tangled. Additionally, in certain embodiments, AED 100 lacks a storage compartment for cardiac pads so as to reduce the overall size of the device. The cardiac pads are therefore carried separately by the user. In an example of step 210, the user may retrieve the cardiac pads (e.g., from a pocket, storage container, or other location) and plug the cardiac pads into AED 100 via a pads connector 310 (see FIG. 5).

In a step 220, the AED is powered on. In an example of step 220, AED 100 may be powered on via a power-on button or switch. In embodiments, AED 100 includes a first button 331 that may be configured as a power button for powering AED 100 on or off, as described below in connection with FIGS. 3 and 4. In some embodiments, plugging in the cardiac pads into the AED automatically powers on the AED. For example, plugging in cardiac pads 122 via pads connector 310 into AED 100 may trigger a switch that automatically powers on AED 100 in step 220. For example, a power switch adjacent pads connector 310 may be actuated by a plug of the cardiac pads 122 when the cardiac pads 122 are plugged into connector 310. In another example, AED 100 may sense the cardiac pads 122 being plugged in by a change in impedance within AED 100 circuitry. For example, without pads 122 plugged in a default impedance level is detected; when pads 122 are plugged in the impedance between the pads changes from the default impedance level, which may be used by controller 110 to power on AED 100; and, when the pads are attached to a patient, the measured impedance level may be used to adjust the applied shock according to patient impedance characteristics.

In embodiments, AED 100 is configured for use by a professional responder who has been trained in the operation of AED 100. As such, AED 100 may include different firmware for powering AED 100. For example, AED 100 may only on be powered on when manually turned on to conserve battery power, rather than remaining powered on in a standby mode. However, a minimal amount of electrical power may be drawn for essential components such as the controller (e.g., for receiving and sending status pings) in a "sleep" state when AED 100 is powered off.

In an optional step 222, method 200 indicates that the AED is powered on. In an example of step 222, controller 110 determines that AED 100 is powered on and sends a signal to UI 150, which provides an indication that the power is on. The indication may comprise an audible sound (e.g., a beep) and/or a visual indication (e.g., an illuminated light), which confirms to a user that AED 100 has been turned on. Optionally, AED 100 may automatically perform additional self-checks when the AED is powered on, and UI 150 may provide additional indications as to the readiness of AED 100. The self-checks may include a state of the cardiac pads (dry, old, used, etc.), a battery level, an electrical circuitry status, or a software/firmware version, for example.

In an optional step 224, an impedance between the cardiac pads is measured. After the cardiac pads 122 are plugged in and AED 100 is powered on, the user may place the cardiac pads 122 on a patient's chest in either the anterior/posterior placement or the anterior lateral placement. The controller 110 then acquires and analyzes the cardiac rhythm of the patient via sensors in the cardiac pads 122. In an example of step 224, an impedance between the cardiac pads 122 is acquired by the controller 110. When the cardiac pads 122 are placed on a patient's body, the impedance measurement relates to the patient's size, and may be used for determining an amount of electrical shock to deliver to the patient. Data regarding body impedance is used to calculate and adjust the appropriate shock waveform via controller 110. For example, the energy output from shock generating electronics 124 may be adjusted according to the body impedance to produce a waveform according to the accepted standard biphasic pattern used in modern defibrillators. In certain embodiments, the voltage waveform is generally between 120-200 Joules in total energy. In some embodiments, optional step 224 is omitted from method 200 and the voltage waveform that is produced is based on an average sized adult.

Controller 110 may also monitor a condition of the cardiac pads 122 by measuring a face-to-face pads impedance, for example. Increased impedance across pads 122 may indicate that the adhesives for attaching the pads 122 to the patient experiencing a cardiac event may be overly dry, thus requiring replacement to maintain effective operation. Controller 110 may determine when the face-to-face pads impedance exceeds a predetermined value and provide an indication to the user via UI 150. In certain embodiments, controller 110 may instruct the user to decrease pad impedance by way of adding a viscous liquid material, such as a jelly, to enhance conductivity between pads 122 and the patient.

In a step 230, a battery charge status in monitored. In an example of step 230, power management block 130 monitors a charge status of battery 132 of AED 100, as described above in connection with FIG. 1. In embodiments, power management block 130 does not provide continuous monitoring of battery 132. Instead, only periodic monitoring is provided when AED 100 is turned on, and no monitoring is provided when AED 100 is turned off to conserve charge of battery 132. A trained operator may be trained to manually monitor the charge status of battery 132 (e.g., via first button 331), as described below in connection with FIGS. 3-5.

In an optional step 232, an indication of battery charge status is provided. In an example of step 232, controller 110 determines a charge status of battery 132 via power management block 130 and sends a signal indicative of the charge status to UI 150, which indicates the charge status via a charge status indicator. The indication may comprise an audible sound (e.g., a beep, a series of beeps, or a voice) and/or a visual indication (e.g., an illuminated or blinking light, or an array of lights), which a trained user will have received training to understand. For example, a light may flash to indicate when a low battery charge status is reached. Alternatively, controller 110 transmits a signal for battery charge status to a mobile device (e.g., smartphone) paired via communications block 170 (e.g., Bluetooth®), and the paired mobile device comprises an application configured to display the battery charge status (e.g., percent charged).

In another example of step 232, UI 150 comprises one or more lights associated with first button 331 (see FIGS. 3-4), which may be configured as a power-on button as described below. The one or more lights are configured to illuminate first button 331 in such a way as indicate a charge status of the battery. For example, the button may be brightly lit, dimly lit, or unlit; the button may blink rapidly, slowly, or not at all; the button may be illuminated with different colors; or the charge status may be conveyed via any combination of these options.

In a step 240, shock generating electronics are charged. In an example of step 240, controller 110 sends a signal to shock generating electronics 124 to initiate charging from battery 132. In embodiments, shock generating electronics 124 include one or more capacitors configured to store an electrical charge for at least one electrical defibrillation. Shock generating electronics 124 may further include a biphasic truncated exponential power stage, as described in the aforementioned U.S. Pat. No. 11,103,718, which is incorporated by reference.

In an optional step 246, a ready-to-shock indication is provided. In an example of step 246, controller 110 determines a status of shock generating electronics 124 and sends a signal indicative of the charge status to UI 150. When the charge status is sufficient, UI 150 then provides an audio or visual indication that the AED 100 is ready to administer an electrical shock to the patient. The audio indication may be a beep or series of beeps or a voice command, for example. The visual indication may be a light or an illuminated or blinking light, or an array of lights, for example.

In step 250, vital signs are monitored. In an example of step 250, a patient's vital signs are monitored via cardiac pads. In embodiments, ECG signals are transmitted from cardiac pads 122 to ECG monitoring circuitry 120, which is communicatively coupled with controller 110. Controller 110 monitors the patient's ECG pattern and determines a status of the patient's vital signs. Step 250 may be performed while the shock generating electronics are simultaneously charging in step 240.

In a step 260, a shockable rhythm is determined. In an example of step 260, controller 110 receives ECG signals from cardiac pads 122 and differentiates between "shockable" rhythms and "unshockable" patterns. An associated algorithm may run internally within controller 110 without real-time access to the cloud, or to any attached device such as a smartphone. Such an algorithm is defined, in the present disclosure, as a shock indicator algorithm (SIA). The specific conditions required for differentiation between shockable and unshockable cardiac rhythms, which are identified by the SIA, follow guidance from industry organizations. In an embodiment, the SIA is prioritized above other processing activities within controller 110 such that the SIA interrupts any other processes in controller 110 to commence the shock protocol, to the exclusion of other activities.

When analysis by controller 110 determines that the cardiac rhythm detected is a shockable rhythm, and when the shock generating electronics 124 have been charged, method 200 then proceeds to step 270 to administer a shock to the patient.

In step 270, a shock is administered via the cardiac pads. In an example of step 270, an electrical shock is administered to a patient via cardiac pads 122. The electrical shock may be a biphasic waveform with a precise shape according to precise timing specifications. In some embodiments, delivery of the shock to the patient is automated such that upon charge completion of the shock generating electronics in step 240 combined with a shockable rhythm being detected in step 260, controller 110 instructs AED 100 to deliver the shock. In some embodiments, delivery of the shock to the patient may be manually initiated by the user by pressing a button (e.g., second button 332) or speaking a voice command that is received by controller 110 via the optional microphone. Alternatively, AED 100 is configured for telemedicine and delivery of the shock to the patient is initiated by a remote user via a tethered device (e.g., a smartphone).

Following step 270, method 200 returns to step 230 to monitor the battery charge status. If the battery charge status is sufficient, method 200 may proceed to optional step 232 to provide a notification of battery charge status, to step 240 to charge the shock generating electronics, and to step 250 to monitor vital signs, in preparation for performing another shock if necessary.

Alternatively in step 260, if analysis by controller 110 determines that the cardiac rhythm detected is an unshockable cardiac rhythm, method 200 returns to step 250 to monitor vital signs for a predetermined duration or until the method is ended by a user. For example, AED 100 may remain powered on with the shock generating electronics 124 charged while awaiting further instructions for the predetermined duration (e.g., five or ten minutes). If the method is ended, either at the end of the predetermined duration or by the user, method 200 proceeds to step 280 to safely discharge the shock generating electronics and to step 290 to end.

In a step 265, the controller 110 determines if return of spontaneous circulation (ROSC) has occurred. While monitoring vital signs in step 250, if ROSC is detected via the SIA, controller 110 determines that a shock is not needed and method 200 may proceed to a step 280 to safely discharge the shock generating electronics and to a step 290 to end.

In step 280, the shock generating electronics are safely discharged. In an example of step 280, the shock generating electronics 124 are safely discharged via an internal discharge circuit (e.g., as part of power management block 130) by activating a power resister.

In step 290, method 200 ends. In an example of step 290, AED 100 may automatically power off to conserve battery power. Alternatively, AED 100 may proceed to a standby mode in which the power remains on for a predetermined duration before powering off. For example, AED 100 may remain powered on for one, five, or ten minutes before powering off. A user may turn off AED 100 at any time by pressing and holding the power button for a predetermined duration (e.g., three seconds). In an embodiment, disconnecting (e.g., unplugging) the cardiac pads 122 may automatically turn off the AED 100 after a predetermined duration in a standby mode.

Steps of method 200 may be performed in the order shown in FIG. 2, or the order of steps may be modified without departing from the scope hereof.

Optionally, AED 100 provides voice prompts of how to perform CPR to the user in coordination with the shock protocol. The voice prompts may also provide recommendations for hand placement, compression depth, and compression rate for effective CPR, in accordance with American Heart Association guidelines. As soon as a shockable rhythm is identified, the voice prompt instructs the operator to halt the CPR and initiate a shock to the victim. Once a shock is delivered, the voice prompts may instruct the operator to resume the proper steps of CPR. If ROSC is detected, the user will be prompted to stop CPR.

Controller 110 may transmit data to a tethered mobile device for displaying the patient's vital signs on a screen of the mobile device. The vital signs and cardiac rhythm may also be transmitted to an emergency service dispatch or regional medical center. The sensors on the cardiac pads 122 may detect that CPR is not given at the appropriate rate or compression depth recommended by American Heart Association (AHA) guidelines, and controller 110 may provide a prompt to the operator by voice to adjust accordingly. A video prompt may also be displayed by the connected mobile device. Controller 110 may also prompt the operator if impedance from sensors in the cardiac pads 122 is too high and provide a recommendation for checking and/or reattaching the cardiac pads as necessary. Data regarding the entire event can be monitored for real-time analysis via a tethered device (e.g., smartphone) and data may be saved to the tethered device or AED 100 for post-event comparative analysis.

Figure 5:
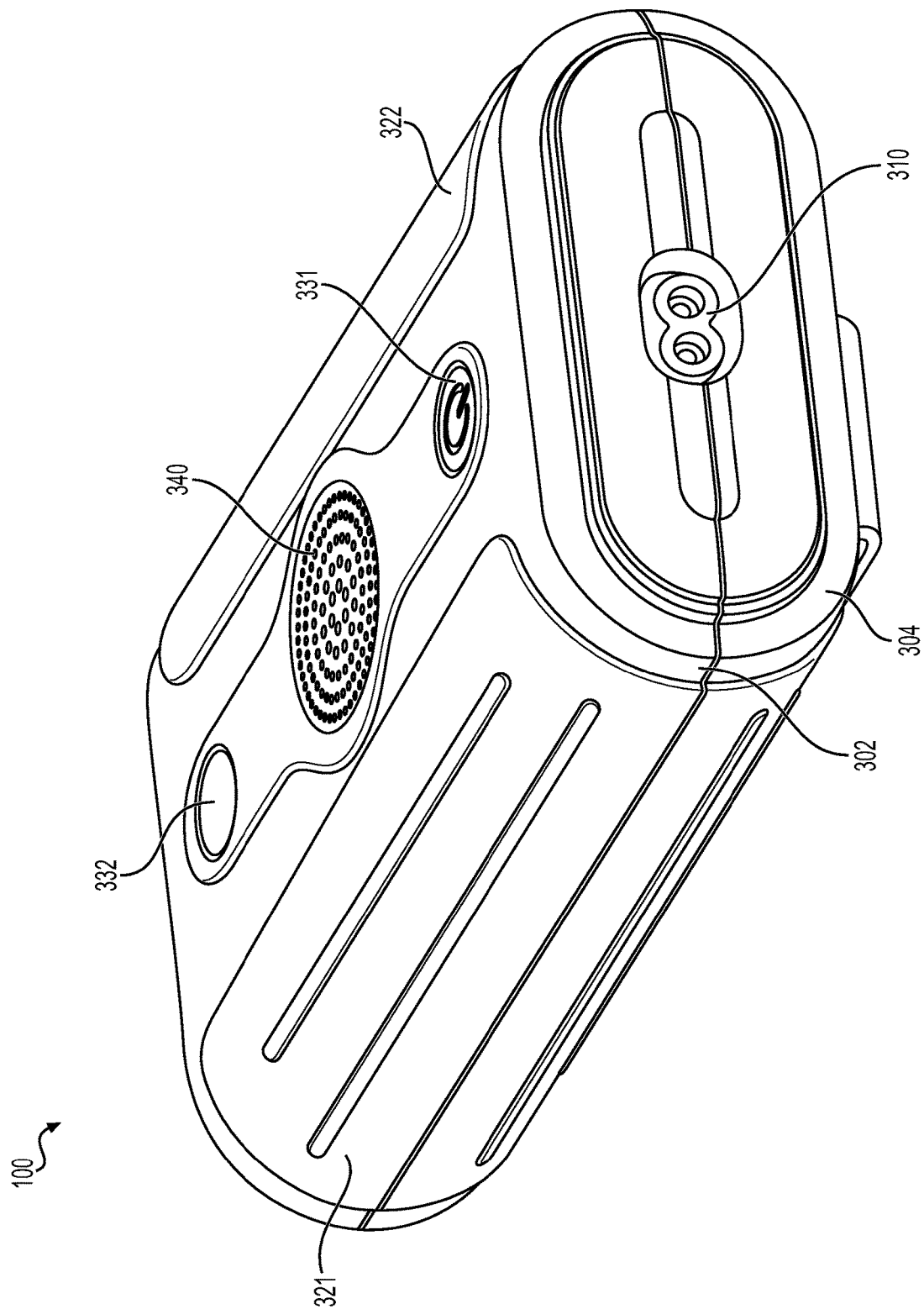
FIG. 5 is yet another perspective view the AED of FIG. 3 showing the front side.
Figure 6:
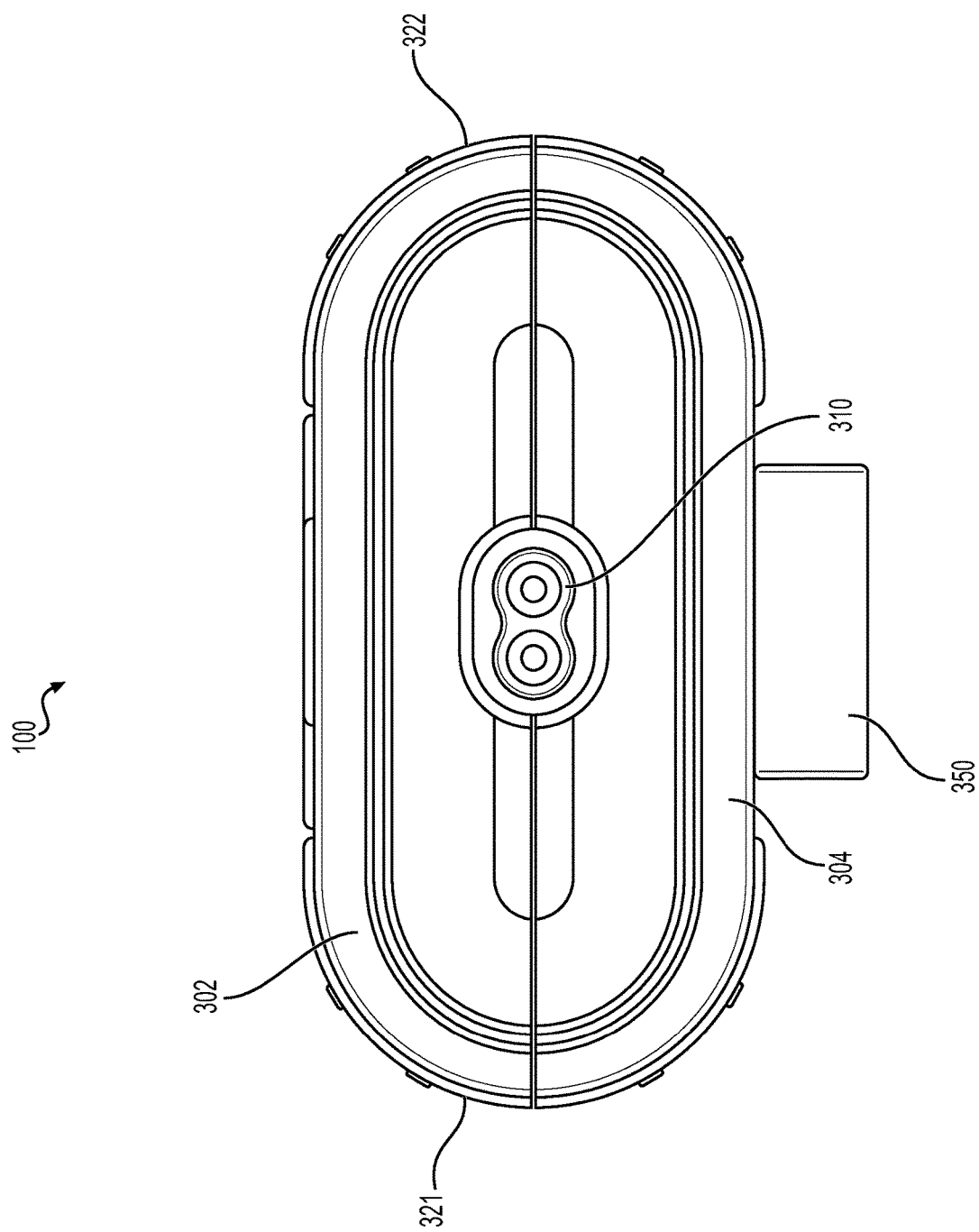
FIG. 6 is a view of a top end of the AED of FIG. 3.

FIGS. 3, 4, and 5 are perspective views of an embodiment of AED 100 showing a front side. FIG. 6 shows a view of a top end of AED 100. FIGS. 3-6 are best viewed together with the following description.

As best viewed in FIGS. 5 and 6, pads connector 310 provides a means of electrically and communicatively coupling cardiac pads (not shown) to AED 100. Pads connector 310 comprises a receptacle accessible on the outside of the outer case of AED 100. Pads connector 310 is configured for electrically and communicatively coupling at least two cardiac pads to AED 100 via wires. The pad wires may be physically coupled together at their terminus for easily plugging both wires into connector 310 simultaneously.

In some embodiments, plugging the cardiac pads 122 into the AED 100 automatically powers on the AED 100. For example, electrically connecting the cardiac pads to AED 100 via pads connector 310 may trigger a switch that automatically powers on AED 100. Alternatively, controller 110 is operable via a minimal amount of battery power so that the controller 110 automatically detects when the cardiac pads are coupled with pads connector 310 (e.g., via a change in impedance), and controller 110 initiates powering on AED 100.

AED 100 is enclosed in an outer case. In embodiments, outer case provides an enclosure that comprises an upper portion 302 and a lower portion 304. The upper and lower portions 302, 304 are made of plastic (e.g., polycarbonate, high-impact polystyrene, acrylonitrile butadiene styrene) via an injection molding process. In embodiments, the plastic material comprises a glow-in-the-dark material to provide illumination in dark settings. The upper and lower portions 302, 304 may be formed together to enclose the internal components of AED 100 via a hot-plate welding seal in which a joint interface between the upper and lower portions 302, 304 is heated to melt and soften the material and then the upper and lower portions 302, 304 are pressed together to form the weld. The resulting outer case provides a waterproof enclosure that has no lip formed on the outer surface. Additionally, no gasket is used, and no bosses or screws are present on the outside of the case.

A first grip 321 and a second grip 322 are formed around opposite outer sides of the outer case. In embodiments, the first and second grips 321, 322 are formed into the outer case during the injection molding process. Alternatively, a grippy material may be fixed to opposite sides of the outer case to provide first and second grips 321, 322. A width and thickness of AED 100 is configured for fitting into the palm of a user's hand such that the user may comfortably hold AED 100 in one hand. First and second grips 321, 322 provide a grippy surface that enables a user to easily hold AED 100 securely in one hand. Due to the small size of AED 100 and the grippy surfaces on the outer case that are provided by first and second grips 321, 322, AED 100 is a hand-carryable device that lacks a separate handle for carrying the device by hand. The absence of a handle further reduces the overall size of AED 100. For example, AED 100 may be about 40% smaller than existing AEDs.

UI 150 may include one or more buttons for enabling a user to operate AED 100. In the embodiment depicted in FIGS. 3 and 4, a first button 331 and a second button 332 are included. First button 331 may be a power on/off button, which enables a user to power on or off the device by depressing the first button 331. Additionally, or alternatively, first button 331 may be a battery charge status button that enables a user to input a request regarding the battery's charge status. In some embodiments, first button 331 is configured as both a power button and a charge status button. For example, pressing first button 331 while AED is powered off will power on the device. Once AED 100 is powered on, pressing first button 331 for a short duration (e.g., two seconds or less) and releasing the button will send a request to power management block 130 via controller 110 for a status of battery 132. Pressing first button 331 for a longer duration (e.g., three seconds) will send a signal to controller 110 to power off AED 100. In some embodiments, first button 331 may be used as a power on button and the device is powered on automatically when the cardiac pads 122 are plugged into connector 310 and powered off automatically when the cardiac pads 122 are unplugged from connector 310.

In embodiments, first button 331 and second button 332 may be configured to be illuminated to provide indications to the user in association with UI 150, FIG. 1. For example, first button 331 may be capable of being illuminated for indicating a power status of AED 100. In this example, first button 331 may include a transparent or semi-transparent outer surface and a light source, such as a light-emitting diode (LED), beneath the outer surface. The light source may illuminate first button 331 upon being depressed to indicate that AED 100 is powered on or to provide a charge status of battery 132. By pressing and holding first button 331 again, AED 100 is powered off and the optional light source turns off to indicate a power off status. In embodiments, first button 331 is depressed for a predetermined duration (e.g., three seconds) before the power status of AED 100 is switched on or off.

Second button 332, in embodiments, is configured as a shock button. For example, pressing second button 332 a first time may initiate charging of the shock generating electronics 124, and pressing second button 332 again after the shock generating electronics 124 have been charged administers a shock to a patient via cardiac pads 122. Alternatively, the shock generating electronics 124 may be automatically charged after sufficient battery charge status is confirmed, for example in step 230 of method 200.

In embodiments, second button 332 provides a shock-initiating button that enables a user to initiate a shock to a patient via the cardiac pads. By depressing second button 332 for a predetermined duration (e.g., two seconds), a signal is sent to controller 110. If controller 110 has determined that battery 132 has a sufficient charge, controller 110 may initiate a charging sequence by instructing AED 100 to charge the shock generating electronics 124 via battery 132. Optionally, controller 110 may also confirm that cardiac pads 122 are connected to AED 100 via pads connector 310. Alternatively, in some embodiments, delivery of the shock to the patient is automated such that controller 110 instructs AED 100 to deliver the shock once the shock generating electronics 124 are fully charged and a shockable rhythm is detected. In yet other embodiments, AED 100 is configured for telemedicine and delivery of the shock to the patient is initiated by a remote user via a tethered device (e.g., a smartphone).

Like first button 331, second button 332 may also be integrated with UI 150 for providing indications to the user. For example, second button 332 may include a transparent or semi-transparent outer surface and a light source underneath for illuminating the outer surface, such that second button 332 is capable of being illuminated. Illumination of second button 332 may be used to indicate a status of the shock generating electronics 124 while being charged. For example, when controller 110 initiates a charging sequence (e.g., following depression of second button 332 by a user), the light source of second button 332 may be intermittently illuminated in a blinking state to indicate charging is in progress. Upon completion of the charging sequence, the light source of second button 332 may be constantly illuminated to indicate that AED 100 is ready to provide a shock via the cardiac pads 122. The user may then depress second button 332 for a predetermined duration, which triggers a signal to be sent to the controller 110, and the controller 110 initiates the shock sequence.

The light source employed in first button 331 and second button 332 may include more than one light (e.g., a plurality of LEDs) of different colors that are used to indicate more than one status. For example, a red light may be employed to illuminate first button 331 to indicate insufficient battery charge, while a green light may be employed to illuminate first button 331 to indicate sufficient battery charge. When a user depresses first button 331 to power on AED 100, the appropriate light is illuminated based on the charge status of battery 132. Other light colors may be employed without departing from the scope hereof.

Different color lights may also be used with second button 332. For example, a first light (e.g., a yellow light) may be illuminated while the shock generating electronics 124 are being charged, while a second light (e.g., a green light) may be illuminated to indicate that the electronics 124 are sufficiently charged for delivering a shock. Additionally, blinking patterns of lights may be used to provide indications to the user. For example, second button 332 may blink while the shock generating electronics 124 are being charged and remain constantly lit once charging is complete.

UI 150 may also include a speaker. For example, as depicted in FIGS. 3-5, a speaker 340 is located beneath upper portion 302 of the enclosure. A plurality of holes may be provided in upper portion 302 above the speaker for enhancing sound quality outside of the enclosure. The plurality of holes may be covered with a gasket or waterproof membrane to maintain water resistance of AED 100. In embodiments, speaker 340 is about 28 mm diameter and about 4.5 mm thick, weighs about 6 g, and consumes less than 0.5 W of electrical power. Speaker 340 may be used by controller 110 to provide audible signals (e.g., beeps) configured to alert and/or notify a user of AED 100. Speaker 340 may also be used to provide audible commands for assisting a user of AED 100.

Figure 7:
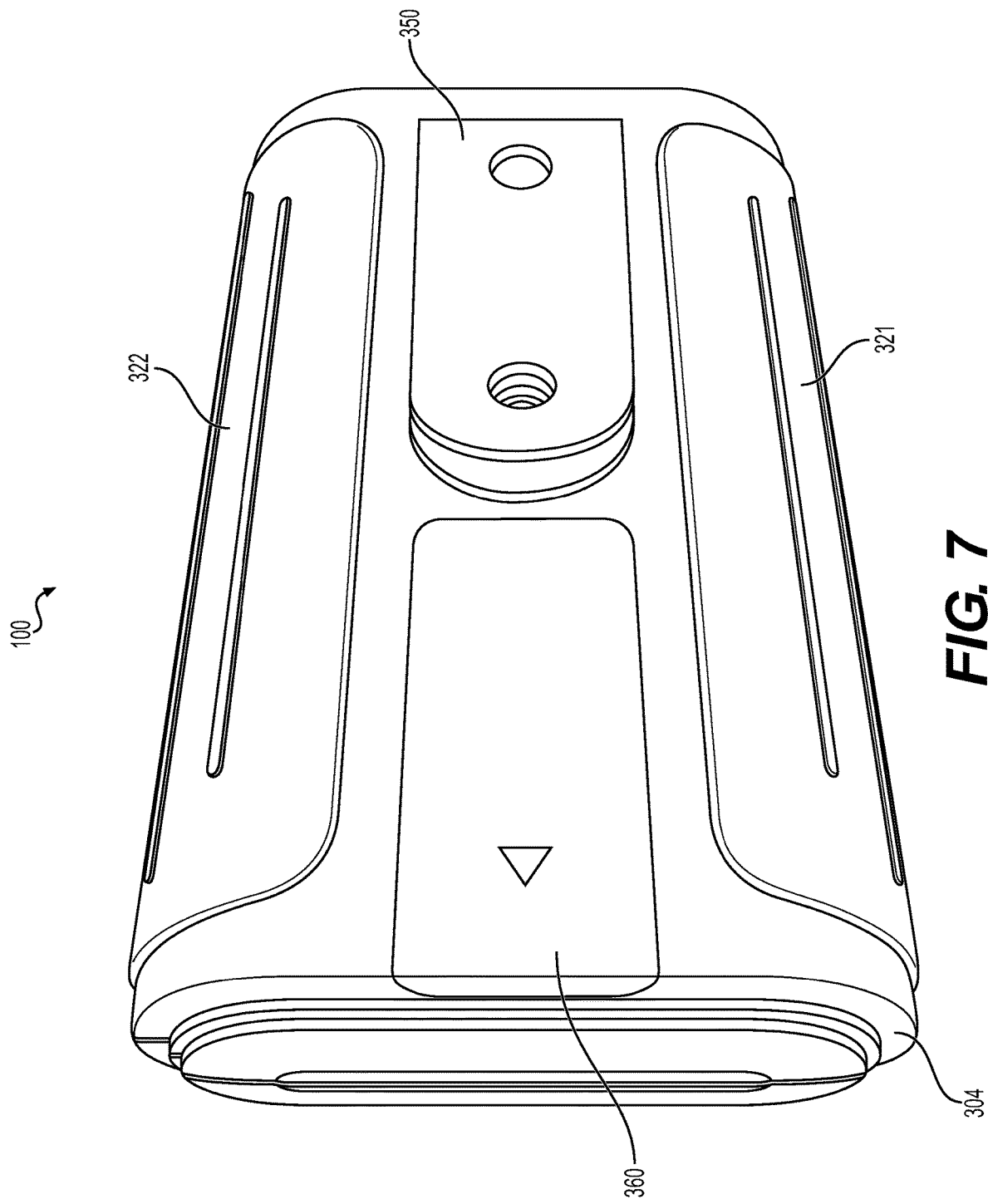
FIG. 7 is a perspective view of the AED of FIG. 3 showing a back side.
Figure 8:
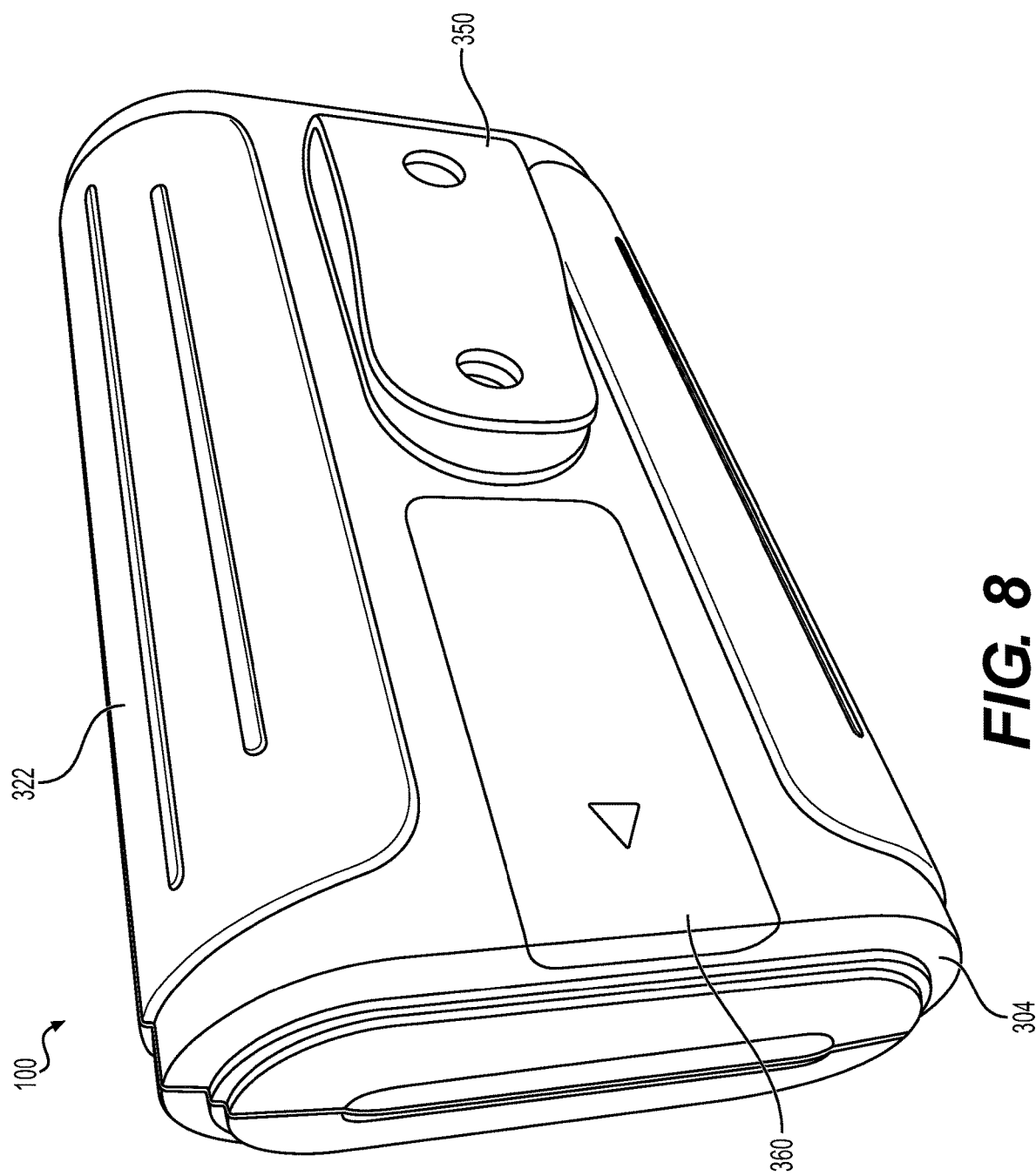
FIG. 8 is another perspective view of the AED of FIG. 3 showing the back side.

FIGS. 7-9 are perspective views of AED 100 showing a back side and a bottom end. A clip 350 (also viewable in FIG. 6) is attached to the back side of AED 100. Clip 350 is, for example, a belt clip configured for clipping on and off of a user's belt or other strap, such as a backpack shoulder strap or waist strap. Clip 350 may also be used to clip AED 100 while being carried in a user's pocket. For example, AED 100 may be stowed in a pants pocket or jacket pocket, and clip 350 may be used to clip an outer fabric of the pocket for securing AED 100 in the pocket. Clip 350 enables AED 100 to be a wearable device by allowing a user to easily clip AED 100 to a belt, strap, or pocket. Due to the small size and low weight (e.g., less than one pound), a user may wear AED 100 routinely without it being an inconvenience. Such sizing and weight of AED 100 may also be advantageous, for example, during physically demanding activities (e.g., biking, running, skiing, etc.) when encountering a SCA event is potentially more likely. In embodiments, AED 100 is between about 15 cm to 17 cm in length, about 4 cm to 5 cm in height, and about 8 cm to 10 cm in width. In certain embodiments, AED 100 is about 160 mm in length, 42 mm in height, and 94 mm in width. However, other dimensions of AED 100 are possible without departing from the scope hereof.

In embodiments, clip 350 is mounted to AED 100 via screws or bolts, which enables its removal (e.g., with a screwdriver or hex driver). In certain embodiments, clip 350 is molded as part of an overmold with lower portion 304. In some embodiments, clip 350 is mounted to AED 100 via a physical mounting shape molded into lower portion 304 (i.e., slot), such that clip 350 may be mounted and removed by simply actuating a portion of the physical mounting shape. Such embodiments may preclude the use of metal for attaching clip 350, which avoids potential for rust in high-humidity environments. A user may prefer to carry AED 100 in a pocket without clip 350 to provide AED 100 with a lower outer profile, which may facilitate slipping AED 100 in and out of the pocket. Also, if the pocket has a zipper, button, snap or other fastening device, clip 350 may not be needed for securing AED 100 within the pocket.

A door 360 is also disposed on the back side of AED 100 as shown in FIGS. 7-9. Door 360 is for example a battery door configured to enclose a battery compartment. In embodiments, the battery compartment is configured for housing and electrically coupling with one or more CR123 batteries. In some embodiments, the battery compartment is configured for housing only one CR123 battery. Door 360 may be slid open and removed for accessing the battery compartment. Alternatively, door 360 may be hinged at one end such that door 360 is swung open via the hinge for accessing the battery compartment. After replacing the one or more batteries, door 360 is reinserted or closed and snapped into place to secure flush with the outer shell of AED 100.

Some non-limiting user scenarios for method 200 are provided below. Method 200 may be configured for use by a trained operator who has received specific training in the operation of AED 100.

In embodiments, AED 100 is configured for use by a professional responder who has been trained in the operation of AED 100. As such, AED 100 may include different firmware for powering AED 100. For example, AED 100 may only on be powered on when manually turned on to conserve battery power, rather than remaining powered on in a standby mode.

In embodiments, power management block 130 does not provide continuous monitoring of battery 132. Instead, only periodic monitoring is provided when AED 100 is turned on, and no monitoring is provided when AED 100 is turned off to conserve battery charge. Rather than providing continuous monitoring of battery 132, which drains the battery, the trained operator of AED 100 is trained to manually check the battery charge status. For example, the operator may press a button to provide an indication of battery charge status, such as first button 331 described above. Alternatively, a tethered device (e.g., a smartphone) may be used to check the battery charge status by the operator.

Additional self-checks of AED 100 may be performed by the trained operator rather than having controller 110 perform automated self-checks. For example, a professional responder such as a EMT may be follow a protocol in which a manual self-check of AED 100 is performed once per work shift. Alternatively, both manual and automated self-checks are provided in embodiments. The self-checks may include a state of the cardiac pads (dry, old, used, etc.), a battery level, an electrical circuitry status, or a software/firmware version, for example. By reducing the amount of automatically monitored features, the complexity and battery power requirements of AED 100 are reduced. In some embodiments, automatic self-checks are performed only at relatively long intervals, such as monthly or when the battery is replaced.

The professional responder may follow a protocol for regular replacement of the battery 132. For example, one CR123 battery would be replaced regularly (e.g., monthly) by the operator.

For backcountry rescue operations, GPS signals from a paired mobile device may be used to determine, for instance, geographical location and altitude. If the paired mobile device is a satellite phone, communication of data from the AED may be made where cellular and Wi-Fi signals are absent.

In embodiments, cardiac pads are placed subcutaneously in a patient and an electronic port extends from the patient's ventricle to outside of the patient to provide an external electronic access for connection to AED 100. The patient may wear AED 100 on their belt via clip 350 or in a pocket, and if a cardiac event occurs, the patient or a person nearby connects AED 100 to the electronic port via pads connector 310. Optionally, extension wires are provided for connecting the electronic port to pads connector 310. One advantage of this configuration is that pacing of the heart directly via the ventricle requires much smaller energy requirements compared to applying a shock via external cardiac pads.

Features described above as well as those claimed below may be combined in various ways without departing from the scope hereof. The following examples illustrate some possible, non-limiting combinations:

(A1) An automated external defibrillator (AED) system includes: shock generating electronics configured to provide at least one electrical shock suitable for a patient experiencing a cardiac event; a battery configured for providing power to the shock generating electronics; power management circuitry configured for managing the shock generating electronics and the battery; a single microprocessor configured for controlling the power management circuitry; an enclosure configured to house the shock generating electronics, the battery, the power management circuitry, and the single microprocessor; and a clip mounted to an exterior of the enclosure, wherein the clip is configured for clipping the AED system to a user's belt for carrying the AED system.

(A2) For the AED system denoted as (A1), the battery may include a single CR123 battery.

(A3) For the AED system denoted as (A1) or (A2), the shock generating electronics may include a capacitor and a quad-phasic power stage configured to charge the capacitor from the single CR123 battery.

(A4) For the AED system denoted as any of (A1) through (A3), the quad-phasic power stage may be configured to charge the capacitor in 90 to 120 seconds.

(A5) For the AED system denoted as any of (A1) through (A4), a first grip and a second grip may be located on opposite outer sides of the enclosure, wherein the first grip and the second grip each provide a grippy surface for assisting with carrying the AED system in one hand without a separate handle.

(A6) For the AED system denoted as any of (A1) through (A5), a pair of cardiac pads may be provided for transmitting an electric shock from the shock generating electronics to a patient, wherein the pair of cardiac pads are configured to be stored separately from the enclosure when not in use.

(A7) For the AED system denoted as any of (A1) through (A6), a pads connector may include a receptacle on the enclosure, wherein the pads connector is configured for electrically and communicatively coupling the pair of cardiac pads with the AED system via wires.

(A8) For the AED system denoted as any of (A1) through (A7), a power switch may be integrated with the pads connector such that plugging in the pair of cardiac pads actuates the power switch to automatically power on the AED system.

(A9) For the AED system denoted as any of (A1) through (A8), a user interface may be provided, wherein the user interface includes a first button, the first button being configured as a power button for enabling the AED system to be powered on or off.

(A10) For the AED system denoted as any of (A1) through (A9), the first button may be further configured as a battery charge status button for receiving a request for the battery charge status when the AED system is powered on.

(A11) For the AED system denoted as any of (A1) through (A10), the first button may include a first light indicator, the first light indicator being configured to indicate a power status of the AED system.

(A12) For the AED system denoted as any of (A1) through (A11), the first light indicator may be further configured as a charge status indicator for indicating a charge status of the battery.

(A13) For the AED system denoted as any of (A1) through (A12), the user interface may further include a second button, the second button being configured as a shock button for administering a shock to the patient.

(A14) For the AED system denoted as any of (A1) through (A13), the second button may be further configured for initiating charging of the shock generating electronics prior to administering a shock to the patient.

(A15) For the AED system denoted as any of (A1) through (A14), the second button includes a second light indicator, the second light indicator being configured to indicate a charge status of the shock generating electronics.

(B1) A method for using an external defibrillator (AED) system, the AED system including shock generating electronics, a single battery configured for providing power to the shock generating electronics, power management circuitry configured for managing the shock generating electronics and the battery, and a single microcontroller configured for controlling the power management circuitry, an enclosure and a clip mounted to an exterior of the enclosure, the method includes: plugging cardiac pads into a connector on the exterior of the enclosure; automatically powering on the AED system when the cardiac pads are plugged into the connector; monitoring a charge status of the battery; monitoring vital signs via the cardiac pads; charging the shock generating electronics; determining whether a shockable rhythm exists; and administering a shock to a patient experiencing a cardiac event via the cardiac pads when the shockable rhythm exists.

(B2) For the method denoted as (B1), charging the shock generating electronics may occur in 90 to 120 seconds via the single battery.

(B3) For the method denoted as (B1) or (B2), the method may further include: determining whether return of spontaneous circulation has occurred while monitoring vital signs via the cardiac pads; and safely discharging the shock generating electronics when return of spontaneous circulation has been determined.

(B4) For the method denoted as any of (B1) through (B3), the method may further include: measuring an impedance between the cardiac pads on the patient; and determining an amount of electrical shock to deliver based on the impedance.

(B5) For the method denoted as any of (B1) through (B4), the method may further include: measuring a face-to-face pads impedance between the cardiac pads; determining whether the face-to-face pads impedance exceeds a predetermined value via the controller; and providing an indication to the user that the face-to-face pads impedance exceeds the predetermined value.

Although the invention has been described with reference to the embodiments illustrated in the attached drawing figures, it is noted that equivalents may be employed and substitutions made herein without departing from the scope of the invention as recited in the claims.

What is claimed is:

1. An automated external defibrillator (AED) system, comprising:
   a stand-alone AED device, comprising:
      shock generating electronics configured to provide at least one electrical shock suitable for a patient experiencing a cardiac event;
      a battery configured for providing power to the shock generating electronics;
      power management circuitry configured for managing the shock generating electronics and the battery;
      a single microprocessor configured for controlling the power management circuitry;
      an enclosure configured to house the shock generating electronics, the battery, the power management circuitry, and the single microprocessor, wherein the enclosure lacks a digital screen;
      a clip mounted to an exterior of the enclosure, wherein the clip is configured for clipping the AED system on and off a user's belt, strap or pocket for carrying the AED system; and
      a pads connector comprising a receptacle accessible on the enclosure, wherein the pads connector is configured for electrically and communicatively coupling the pair of cardiac pads with the stand-alone AED device via wires; and
   a pair of cardiac pads for transmitting an electric shock from the shock generating electronics to a patient, wherein the pair of cardiac pads are configured to be stored separately from the enclosure when not in use; and
   a power switch integrated with the pads connector such that plugging in the pair of cardiac pads actuates the power switch to automatically power on the AED stand-alone device and unplugging the pair of cardiac pads actuates the power switch to automatically power off the stand-alone AED device.

2. The AED system of claim 1, wherein the battery comprises a single CR123 battery.

3. The AED system of claim 1, wherein the shock generating electronics comprise a capacitor and a quad-phasic power stage configured to charge the capacitor from the single CR123 battery.

4. The AED system of claim 3, wherein the quad-phasic power stage is configured to charge the capacitor in 90 to 120 seconds.

5. The AED system of claim 1, further comprising a first grip and a second grip located on opposite outer sides of the enclosure, wherein the first grip and the second grip each provide a grippy surface for assisting with carrying the AED system in one hand, and wherein the enclosure lacks a separate handle for carrying the AED system.

6. The AED system of claim 1, further comprising a user interface, wherein the user interface comprises a first button, the first button being configured as a power button for enabling the AED system to be powered on or off.

7. The AED system of claim 6, wherein the first button is further configured as a battery charge status button for receiving a request for the battery charge status when the AED system is powered on.

8. The AED system of claim 6, wherein the first button comprises a first light indicator, the first light indicator being configured to indicate a power status of the AED system.

9. The AED system of claim 8, wherein the first light indicator is further configured as a charge status indicator for indicating a charge status of the battery.

10. The AED system of claim 6, wherein the user interface further comprises a second button, the second button being configured as a shock button for administering a shock to the patient.

11. The AED system of claim 10, wherein the second button is further configured for initiating charging of the shock generating electronics prior to administering a shock to the patient.

12. The AED system of claim 10, wherein the second button comprises a second light indicator, the second light indicator being configured to indicate a charge status of the shock generating electronics.

13. The AED system of claim 1, wherein the power switch comprises a physical switch located adjacent to the pads connector, and the power switch is configured to be actuated by a plug of the cardiac pads when the cardiac pads are plugged into the pads connector.

14. The AED system of claim 1, wherein the controller determines that the cardiac pads have been plugged in based on a change in an impedance level within the shock generating electronics, and the controller powers on the stand-alone AED device upon determining that the cardiac pads have been plugged in.

15. The AED system of claim 1, wherein the enclosure comprises an outer case formed from two halves via a hot-plate welding seal such that the outer case lacks bosses and no lip exists on an outer surface of the enclosure.

16. The AED system of claim 15, wherein the enclosure is waterproof and lacks a gasket or screws on the outer case.

17. The AED system of claim 1, wherein the clip comprises a removable clip configured for being easily added or removed from the enclosure.

* * * * *